United States Patent [19]
Bauer et al.

[11] Patent Number: 5,656,688
[45] Date of Patent: Aug. 12, 1997

[54] CARBAMOYLHYDROXYLAMINES AND POLYMER-CONTAINING SOLUTION OR DISPERSION THEREOF

[75] Inventors: Gerhard Bauer, Weinheim; Karl Haeberle, Speyer; Roland Baumstark, Neustadt; Kaspar Bott, Mannheim, all of Germany

[73] Assignee: BASF Aktiengesellschaft, Ludwigshafen, Germany

[21] Appl. No.: 535,054

[22] PCT Filed: Apr. 25, 1994

[86] PCT No.: PCT/EP94/01283

§ 371 Date: Oct. 30, 1995

§ 102(e) Date: Oct. 30, 1995

[87] PCT Pub. No.: WO94/25433

PCT Pub. Date: Nov. 10, 1994

[30] Foreign Application Priority Data

May 4, 1993 [DE] Germany ............ 43 14 623.6

[51] Int. Cl.$^6$ ............ C08L 39/00; C08L 75/00; C08F 8/32; C07C 271/00
[52] U.S. Cl. .......... 524/555; 156/331.7; 252/182.2; 252/183.11; 252/312; 428/423.1; 525/125; 525/127; 525/379; 528/905; 560/157; 560/158; 560/159
[58] Field of Search ............ 252/312, 182.2, 252/183.11; 525/127, 125, 379; 528/905; 156/331.7; 428/423.1; 560/156, 157, 158, 165; 524/555

[56] References Cited

U.S. PATENT DOCUMENTS

| | | | |
|---|---|---|---|
| 3,926,875 | 12/1975 | Tsugukuni et al. | 525/127 X |
| 4,352,858 | 10/1982 | Stanley | 428/423.1 |
| 4,396,738 | 8/1983 | Powell et al. | 524/228 |
| 4,722,969 | 2/1988 | Huynh-Tran et al. | 525/127 X |
| 5,028,682 | 7/1991 | Witzeman et al. | 428/423.1 |
| 5,296,160 | 3/1994 | Tirpak et al. | 252/182.2 |

FOREIGN PATENT DOCUMENTS

| | | |
|---|---|---|
| 0003516 | 8/1979 | European Pat. Off. |
| 0244355 | 11/1987 | European Pat. Off. |
| 0516074 | 12/1992 | European Pat. Off. |
| 0522306 | 1/1993 | European Pat. Off. |
| 3112117 | 10/1982 | Germany . |
| 3521618 | 12/1986 | Germany . |
| 3807555 | 9/1988 | Germany . |
| 4219384 | 12/1993 | Germany . |

OTHER PUBLICATIONS

Database WPI, Derwent Publications, AN 79–619188/34, GB 1550811, Aug. 22, 1979.

*Primary Examiner*—Richard D. Lovering
*Attorney, Agent, or Firm*—Oblon, Spivak, McClelland, Maier & Neustadt, P.C.

[57] ABSTRACT

A compound of the formula

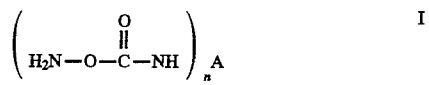

where A is an n-valent organic radical and n is an integer greater than 1.

5 Claims, No Drawings

CARBAMOYLHYDROXYLAMINES AND POLYMER-CONTAINING SOLUTION OR DISPERSION THEREOF

This application is a 371 of PCT/EP94/01283 filed Apr. 25, 1994.

The present invention relates to a compound of the formula

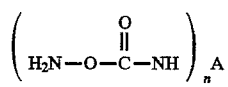

where A is an n-valent organic radical and n is an integer greater than 1, or a salt thereof.

The present invention furthermore relates to dispersions or solutions of free radical polymers, polycondensates or polyadducts which contain compounds of the formula I.

Copolymers which are used in coating materials or adhesives are often crosslinkable copolymers. As a result of crosslinking, for example, it is possible to obtain protective coatings or adhesive coatings having good elastic properties, high cohesion, ie. internal strength, and high resistance to chemicals and to solvents.

The copolymers are crosslinked in general by adding a crosslinking agent, which reacts with functional groups in the copolymer.

Possible crosslinking agents are, for example, polyisocyanates, which react with hydroxyl or amino groups.

DE-A-35 21 618 discloses corresponding aqueous adhesive formulations in which polyisocyanates dispersed in water are added, as crosslinking agents, to aqueous dispersions of copolymers obtained by free radical polymerization. Similar adhesive formulations are also described in U.S. Pat. No. 4,396,738 and DE-A-31 12 117.

However, the disadvantage of these aqueous formulations is the poor shelf life. Hence, the polyisocyanate may be dispersed in water and mixed with the copolymer only shortly before said polyisocyanate is used as a crosslinking agent.

A longer shelf life can be achieved by reacting the isocyanate groups with blocking agents, for example oximes, caprolactam, phenols or dialkyl maleates. The blocked polyisocyanates obtained undergo hydrolysis in aqueous dispersion only to a minor extent.

DE-A-38 07 555 relates to such a diisocyanate which is blocked with oximes and dispersed in water and is suitable as an additive for polymers dispersed in water.

However, crosslinking reactions occur only after elimination of the blocking agent at above about 130° C.

Aqueous adhesive formulations known to date and containing polyisocyanates as crosslinking agents thus either have a short shelf life and can therefore be used only as a 2-component system or crosslink only at high temperatures.

Aqueous dispersions which have a long shelf life and crosslink at room temperature after removal of the solvent are disclosed in EP-A-3516. These dispersions contain polyhydrazides which react with monomers polymerized in the copolymer and having carbonyl groups.

German Patent Application P 42 19 384.2 discloses oxime ethers as crosslinking agents. EP-A-516 074 describes aminooxy derivatives as crosslinking agents for copolymers containing keto or aldehyde groups.

EP-A-522 306 describes oxime-blocked polyisocyanates as crosslinking agents for carbonyl-containing polymers.

There is in principle a need for further dispersions crosslinking at room temperature, in order to be able to provide alternatives to polyhydrazide crosslinking. Furthermore, these dispersions should have good performance characteristics, for example good adhesion, in particular wet adhesion to a very wide range of substrates.

It is an object of the present invention to provide dispersions or solutions of crosslinkable copolymers, which dispersions or solutions have a long shelf life, contain a crosslinking agent and are crosslinkable at room temperature.

We have found that this object is achieved by the compound defined above, as well as dispersions or solutions which contain this compound.

The compound of the formula I is suitable as a crosslinking agent or adhesion promoter in dispersions or solutions of free radical polymers, polycondensates or polyadducts.

The crosslinking of free radical polymers, polycondensates or polyadducts containing keto or aldehyde groups with crosslinking agents of the formula I takes place on removal of the liquid phase of the dispersion or solution.

In the formula I, A is an n-valent organic radical, preferably an aliphatic or araliphatic hydrocarbon radical of 4 to 20, preferably 4 to 10, carbon atoms, very particularly preferably an aliphatic radical.

A may also be an organic radical which contains, for example, urethane, urea, biuret, isocyanurate or uretdione groups and preferably has a molecular weight of up to 10,000, particularly preferably up to 1,000, g/mol. A is generally derived from diisocyanates or polyisocyanates, ie. A corresponds to the di- or polyisocyanates without the isocyanate groups.

n is preferably an integer of from 2 to 20, particularly preferably from 2 to 10, very particularly preferably from 2 to 4.

Starting components for the preparation of the compound I are polyisocyanates.

Examples of polyisocyanates are diisocyanates, such as tetramethylene diisocyanate, hexamethylene diisocyanate (HDI), dodecamethylene diisocyanate, 1,4-diisocyanatocyclohexane, 4,4'-di-(isocyanatocyclohexyl)-methane (HMDI), trimethylhexane diisocyanate, 1-isocyanato-3,3,5-trimethyl-5-isocyanatocyclohexane (IPDI), 2,4- and 2,6-diisocyanatotoluene (TDI), tetramethylxylylene diisocyanate, p-xylylene diisocyanate, 2,4'- and 4,4'-diisocyanatodiphenylmethane, and, for example, polyisocyanates having isocyanurate or biuret groups, in particular those based on 1,6-diisocyanatohexane and/or on 1-isocyanato-3,3,5-trimethyl-5-isocyanatomethylcyclohexane, or reaction products of polyisocyanates with polyhydric, in particular dihydric to pentahydric, alcohols. Aliphatic alcohols having a total of 2 to 8 carbon atoms, such as ethylene glycol, 1,4-butanediol, 1,2-propanediol, glycerol, trimethylolpropane or pentaerythritol, are preferred.

Polyisocyanates modified to give them hydrophilic properties are also suitable. These are self-dispersing in water so that dispersing can be carried out substantially without emulsifiers and dispersants. Self-dispersible polyisocyanates having nonionic hydrophilic groups, in particular reaction products of polyisocyanates with polyalkylene ether alcohols, as described in, for example, EP-A-206 059, are known. Polyisocyanates become self-dispersible also through incorporation of ionic groups or of groups convertible into ionic groups. Such polyisocyanates are disclosed in, for example, DE-A-41 13 160 and DE-A-40 01 783.

Hexamethylene diisocyanate, IPDI and HMDI and mixtures thereof, as well as the derivatives obtained therefrom and having higher functionality, are preferably used.

The isocyanate groups of the polyisocyanates are blocked with oximes or hydroxamic esters according to the known blocking reactions a)

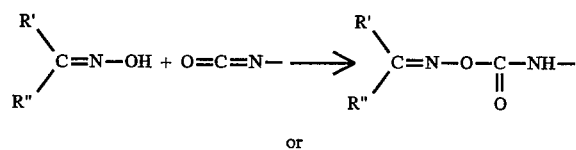

or b)

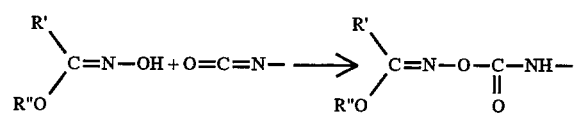

Suitable oximes are those of aliphatic, cycloaliphatic or aromatic aldehydes or ketones, for example acetone oxime, methyl ethyl ketoxime, diethyl ketoxime, methyl isopropyl ketoxime, methyl isobutyl ketoxime, diisopropyl ketoxime, cyclohexanone oxime, 2-methylcyclohexanone oxime, 2,6-dimethylcyclohexanone oxime, acetophenone oxime, benzophenone oxime or diethyl glyoxime. Oximes of aliphatic ketones having one keto group and a total of 3 to 12 carbon atoms, in particular acetone oxime and methyl ethyl ketoxime, are preferred. Preferred hydroxamic esters are those in which the above variables R' and R" are each $C_1$–$C_5$-alkyl and R' may furthermore be H.

The blocked polyisocyanates can be prepared in a manner known to the skilled worker, in inert organic solvents, for example aromatic hydrocarbons, such as toluene, or in the absence of solvents, at from 20° to 150° C., preferably from 20° to 100° C.

The ratio of isocyanate groups of the polyisocyanates used to the oximes or hydroxamic esters is preferably from 1:0.9 to 1:1.4, particularly preferably from 1:0.95 to 1:1.1.

The blocking reaction can advantageously be carried out in the presence of metal salts as catalysts, for example dibutyltin dilaurate or tin octoate.

The blocked polyisocyanates are then hydrolytically cleaved in the presence of water and strong acids having an acid constant of $>10^{-2}$, preferably $>10^{-1}$ (cf. Anorganikum, Berlin 1977, page 458), into the compounds of the formula I. A particularly preferably used acid is hydrochloric acid. The compounds of the formula I which are obtained as cleavage products are in the form of salts or hydrochlorides (amino groups are protonated). The free compounds of the formula I can, if desired, be obtained by suitable measures for deprotonation, for example by the addition of bases. The cleavage reaction is preferably carried out at reaction temperatures of from 0° to 60° C., preferably 20° to 35° C. The reaction temperature can be kept surprisingly low compared with usual temperatures in the hydrolytic cleavage of, for example, oxime ethers (cf. also Houben-Weyl, Methoden der organischen Chemie, Vol. 10, 1, page 1186).

If the polyisocyanates blocked by oximes are used for preparing the compounds having the structure I, it is advantageous to remove the ketone or aldehyde formed in the cleavage by evaporation from the reaction mixture, in order to achieve a satisfactory conversion. When polyisocyanates blocked with hydroxamic esters are used, the reaction equilibrium is in general completely on the side of the cleavage products, so that separating off the ketones or aldehydes has hardly any additional advantages. It is advantageous to add a solvent or precipitating agent, eg. diethyl ether, in which the product is sparingly soluble and can therefore be precipitated.

The compound of the formula I can be added to dispersions or solutions of free radical polymers, polyadducts or polycondensates as crosslinking agents or for improving the adhesion.

The compound of the formula I is particularly suitable as a crosslinking agent for a polymer, polycondensate or polyadduct which contains from 0.001 to 20, preferably from 0.01 to 10, very particularly preferably from 0.05 to 4, % by weight of aldehyde groups (CHO) or keto groups (CO) and is present in solution or dispersion.

This may be, for example, a copolymer obtained by free radical polymerization, a polyester as a polycondensate condensate or a polyurethane as a polyadduct.

In the case of the copolymers obtained by free radical polymerization, the aldehyde or keto groups are preferably incorporated by polymerizing ethylenically unsaturated compounds which contain these groups.

They are preferably ethylenically unsaturated compounds having one or two aldehyde or keto groups or one aldehyde and one keto group and an olefinic double bond capable of undergoing free radical polymerization (referred to below as monomers a)).

In the case of a polyester, they are, for example, monoalcohols, diols, monocarboxylic acids or dicarboxylic acids, and in the case of a polyurethane they may be, for example, mono- or diisocyanates or likewise monoalcohols or diols, which contain aldehyde or keto groups.

Examples of monoalcohols are hydroxyacetone, hydroxybenzaldehyde, acetoin and benzoin.

Examples of suitable monocarboxylic acids are ketocarboxylic acids, such as pyruvic acid or levulinic acid.

Keto-containing polyurethane dispersions are disclosed, for example, in DE-A-38 37 519, EP-A-332 326 and EP-A-442 652.

Furthermore, compounds having aldehyde or keto groups may not only be bound as components of the main chain in the polymers, polycondensates or polyadducts but, by reaction with reactive groups in the polymer main chain, may also be bound to the polymers, polycondensates or polyadducts.

A copolymer obtained by free radical polymerization and consisting of the monomers a) which contain aldehyde or keto groups and further monomers b) and c) is preferred.

Examples of suitable monomers a) are acrolein, methacrolein, vinyl alkyl ketones where the alkyl radical is of 1 to 20, preferably 1 to 10, carbon atoms, formylstyrene and alkyl (meth)acrylates where the alkyl radical has one or two keto or aldehyde groups or one aldehyde and one keto group and preferably has a total of 3 to 10 carbon atoms, eg. (meth)acryloyloxyalkylpropanals, as described in DE-A-27 22 097. N-Oxoalkyl(meth)acrylamides as disclosed in, for example, U.S. Pat. No. 4,226,007, DE-A-20 61 213 or DE-A-22 07 209 are also suitable.

Acetoacetyl (meth)acrylate, acetoacetoxyethyl (meth) acrylate and in particular diacetoneacrylamide are particularly preferred.

The copolymer contains, in particular, from 20 to 99.99, preferably from 60 to 99.9, particularly preferably from 80 to 99.5, % by weight, based on the copolymer, of the main monomers b).

Suitable monomers b) are esters of acrylic or methacrylic acid with alkyl alcohols of 1 to 20 carbon atoms. Examples of such alcohols are methanol, ethanol, n-propanol, isopropanol, n-butanol, sec-butanol, tert-butanol, n-pentanol, isoamyl alcohol, n-hexanol, octanol, 2-ethylhexanol, lauryl alcohol and stearyl alcohol.

Good results are obtained with alkyl (meth)-acrylates having a $C_1$–$C_{10}$-alkyl radical, such as methyl methacrylate, methyl acrylate, n-butyl acrylate, ethyl acrylate and 2-ethylhexyl acrylate.

Mixtures of the alkyl (meth)acrylates are also particularly useful.

Vinyl esters of carboxylic acids of 1 to 20 carbon atoms, such as vinyl laurate, vinyl stearate, vinyl propionate and vinyl acetate, are also suitable.

Suitable vinylaromatic compounds of up to 20 carbon atoms are vinyltoluene, α- and p-styrene, α-butylstyrene, 4-n-butylstyrene, 4-n-decylstyrene and preferably styrene. Examples of ethylenically unsaturated nitriles are acrylonitrile and methacrylonitrile.

The vinyl halides are ethylenically unsaturated compounds substituted by chlorine, fluorine or bromine, preferably vinyl chloride and vinylidene chloride.

Examples of nonaromatic hydrocarbons having 2 to 8 carbon atoms and at least two conjugated olefinic double bonds are butadiene, isoprene and chloroprene.

The monomers b) can be used in particular in the form of a mixture, especially to establish desired glass transition temperatures of the copolymer.

Examples of suitable further copolymerizable monomers c), ie. those not belonging to a) and b), are esters of acrylic and methacrylic acid with alcohols of 1 to 20 carbon atoms which contain at least one further heteroatom in addition to the oxygen atom in the alcohol group and/or which contain an aliphatic or aromatic ring.

Examples are 2-ethoxyethyl acrylate, 2-butoxy-ethyl (meth)acrylate, dimethylaminoethyl (meth)acrylate, diethylaminoethyl (meth)acrylate, aryl, alkaryl or cycloalkyl (meth)acrylates, such as cyclohexyl (meth)-acrylate, phenylethyl (meth)acrylate or phenylpropyl (meth)acrylate, or acrylates of heterocyclic alcohols, such as furfuryl (meth) acrylate.

Other examples are further comonomers, such as (meth) acrylamide and its derivatives substituted in the nitrogen by $C_1$–$C_4$-alkyl.

Comonomers having hydroxyl functional groups, for example $C_1$–$C_{15}$-alkyl (meth)acrylates which are substituted by one or two hydroxyl groups, are also particularly important. Particularly important comonomers of this type are $C_1$–$C_8$-hydroxyalkyl (meth)acrylates, such as n-hydroxyethyl, n-hydroxypropyl or n-hydroxybutyl (meth) acrylate.

The presence of comonomers having salt-forming groups is advisable, for example, for the preparation of self-dispersible copolymers which are suitable, for example, for aqueous secondary dispersions. Comonomers having salt-forming groups are in particular itaconic acid, acrylic acid and methacrylic acid.

The amount of the further comonomers in the copolymer may be in particular from 0 to 50, preferably from 0 to 20, very particularly preferably from 0 to 10, % by weight.

The amounts of the monomers a), b) and c) sum to 100% by weight.

The amount of the monomers a) is chosen so that the copolymer has the abovementioned content of aldehyde or keto groups.

The copolymer is prepared in general by free radical polymerization. Suitable polymerization methods, such as mass, solution, suspension or emulsion polymerization, are known to the skilled worker.

The copolymer is preferably prepared by solution polymerization with subsequent dispersing in water, or particularly preferably by emulsion polymerization, the copolymer being obtained as an aqueous dispersion.

In the emulsion polymerization, the copolymers can be polymerized in the conventional manner in the presence of a water-soluble initiator and of an emulsifier at, preferably, from 30° to 95° C.

Examples of suitable initiators are sodium persulfate, potassium persulfate, ammonium persulfate, tert-butyl hydroperoxides, water-soluble azo compounds and redox initiators.

The emulsifiers used are, for example, alkali metal salts of relatively long-chain fatty acids, alkyl-sulfates, alkylsulfonates, alkylated arylsulfonates or alkylated diphenyl ether sulfonates.

Other suitable emulsifiers are reaction products of alkylene oxides, in particular ethylene oxide or propylene oxide, with fatty alcohols, fatty acids or phenol or alkylphenols.

In the case of aqueous secondary dispersions, the copolymer is first prepared by solution polymerization in an organic solvent and then dispersed in water with the addition of salt formers, for example of ammonia to carboxyl-containing copolymers, without the use of an emulsifier or dispersant. The organic solvent can be distilled off. The preparation of aqueous secondary dispersions is known to the skilled worker and is described in, for example, DE-A-37 20 860.

For adjusting the molecular weight, regulators may be used in the polymerization. For example, —SH-containing compounds, such as mercaptoethanol, mercaptopropanol, thiophenol, thioglycerol, ethyl thioglycolate, methyl thioglycolate and tert-dodecyl mercaptan, are suitable.

The type and amount of the comonomers is expediently chosen so that the copolymer obtained [lacuna] a glass transition temperature of, preferably, from −60° to +140° C. Depending on whether rigid or flexible coatings are desired, high or low glass transition temperatures are obtained by the choice of the monomers. The glass transition temperature of the copolymer can be determined by conventional methods, such as differential thermal analysis or differential scanning calorimetry (cf. for example ASTM 3418/82, ie. midpoint temperature).

The dispersion or solution contains a compound of the formula I as an adhesion promoter or as a crosslinking agent.

The amount of the compound of the formula I in the dispersions of the [sic] solutions is preferably from 0.01 to 30, particularly preferably from 0.1 to 20, very particularly preferably from 0.1 to 5, % by weight, based on the polymer, polycondensate or polyadduct. In the case of free radical polymers, polycondensates or polyadducts containing keto or aldehyde groups, the content is advantageously chosen so that there is a roughly equimolar ratio of the groups

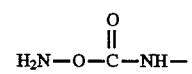

to the keto and/or aldehyde groups.

Metal salts or metal complexes which are present in, or added to, the dispersions or solutions generally do not have an adverse effect on the crosslinking or adhesion promotion by compounds I.

The solids content of the novel dispersion or solution is preferably from 20 to 90, in particular from 30 to 70, % by weight.

The novel dispersions or solutions are suitable as coating materials for various substrates having plastic, wood or metal surfaces or, for example, for textiles, nonwovens, leather or paper. They are also suitable for applications in building chemistry, for example as adhesives, sealing compounds, binders and the like. The coatings may be, for example, decorative coatings, protective coatings or adhesive coatings.

An aqueous dispersion of a copolymer obtained by free radical polymerization, in particular one containing keto and/or aldehyde groups, is particularly suitable for the stated uses.

The aqueous dispersion may also contain organic, preferably water-miscible solvents as auxiliary solvents.

Depending on the intended use, the novel dispersion or solution may contain conventional assistants and additives. These include, for example, fillers, such as quartz powder, quartz sand, finely divided silica, barite, calcium carbonate, chalk, dolomite or talc, which are often used together with suitable wetting agents, for example polyphosphates, such as sodium hexamethaphosphate [sic], naphthalenesulfonic acid or ammonium or sodium polyacrylates, the wetting agents being added in general in an amount of from 0.2 to 0.6% by weight, based on the filler.

If desired, fungicides for preservation are used in general in amounts of from 0.02 to 1% by weight, based on the total dispersions [sic] or solution. Examples of suitable fungicides are phenol derivatives or cresol derivatives or organotin compounds.

The novel dispersions or solutions, especially aqueous dispersions of free radical copolymers, are particularly suitable as sealing compounds or adhesives, in particular, for example, as laminating adhesives for the production of laminated films and high-gloss films. As adhesives, the dispersions may contain, in addition to the abovementioned additives, also special assistants and additives conventionally used in adhesives technology. These include, for example, thickeners, plasticizers and tackifiers, for example natural resins or modified resins, such as rosin esters, or synthetic resins, such as phthalate resins.

Dispersions which are used as adhesives particularly preferably contain alkyl (meth)acrylates as comonomers b) in the copolymer.

For use as an adhesive formulation, the glass transition temperature of the copolymers is preferably brought to values of from 0° to −40° C.

When used as an adhesive or as a binder in coatings, the dispersions surprisingly also exhibit very good adhesion, in particular wet adhesion.

The pH of the dispersion is preferably brought to 2–9, since the crosslinking reaction with the copolymers can be acid-catalyzed.

The novel dispersions or solutions which contain compounds of the formula I have a long shelf life. The crosslinking reaction, for example with keto and/or aldehyde groups, occurs at as low as room temperature on removal of the liquid phase, for example volatilization of the water.

The volatilization of the water can be accelerated by increasing the temperature, for example to 30°–100° C.

In the coating of substrates, it is in principle also possible to apply a dispersion or solution of the polymer, polycondensate or polyadduct which does not contain the compound of the formula I to a surface to which compounds of the formula I have been applied beforehand in a separate operation.

In this case, the compounds act as primers.

After application of the dispersion or solution, the crosslinking then takes place or an improvement in adhesion is observed.

Preparation of the copolymer dispersions
Dispersion 1

400 g of demineralized water, 150 g of feed 1 (see below), 25 g of a 20% strength by weight aqueous solution of a $C_{16}/C_{18}$-fatty alcohol etherified with 18 ethylene oxide units, 5 g of a 20% strength by weight aqueous solution of the disodium salt of p-dodecyl-diphenyl ether disulfonate and 50 g of feed 2 were initially taken in a reaction vessel having a stirrer and two feed vessels (feed 1 and feed 2) and were heated to 85° C. After 15 minutes, feed 1 was added uniformly to the reaction vessel in the course of 2 hours and feed 2 was added uniformly in the course of 2.25 hours. After complete addition of the initiator (feed 2), the dispersion was stirred for a further 2 hours at 85° C.

Feed 1: (stirred during the polymerization)
368 g of demineralized water 50 g of a 20% strength by weight aqueous solution of a $C_{16}/C_{18}$-fatty alcohol etherified with 18 ethylene oxide units (emulsifier)
75 g of a 20% strength by weight aqueous solution of the disodium salt of dodecyldiphenyl ether disulfonate (emulsifier)
38 g of 2-(acetoacetoxy)ethyl methacrylate (AAEM)
30 g of a 50% strength by weight aqueous solution of acrylamide
27 g of methacrylic acid
300 g of methyl methacrylate
700 g of n-butyl acrylate Feed 2:
200 g of demineralized water
5 g of sodium persulfate Dispersion 2

The preparation of dispersion 2 corresponded to that of dispersion 1, except that the methyl methacrylate in feed 1 was completely replaced with styrene. Preparation of the crosslinking agent (VI)

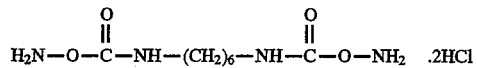

a) Blocking of hexamethylene diisocyanate with acetone oxime 146.2 g (2.0 mol) of acetone oxime were dissolved in 600 g of acetone. 168 g (1.0 mol) of hexamethylene diisocyanate were then added dropwise in the course of 30 minutes. Stirring was carried out overnight, after which 190.3 g of product were filtered off under suction (melting point 94°–96° C.).

b) Hydrolytic cleavage to give O,O'-[(N,N'-hexamethylene)-biscarbamoyl]-hydroxylammonium chloride A mixture of 78.5 g (0.25 mol) of O,O'-[(N,N'-hexamethylene)-biscarbamoyl]-acetone oxime (product from a)), 150 g of concentrated hydrochloric acid and 50 g of water was heated to 35°–38° C. for 5 hours under reduced pressure from a water pump (20–30 mbar). Thereafter, the excess hydrochloric acid and the water were distilled off with 300 ml of 1,2-dichloroethane as entraining agent at reduced pressure (210 mbar) at 37° C. in the course of 3 hours. The product suspended in the entraining agent was filtered off and was dried in the air. Yield 69.8 G [sic] (91% of theory), mp. 114° C. (decomposition).

Elemental analysis:

|  | C | H | O | N | Cl |
|---|---|---|---|---|---|
| Calculated | 31.28 | 6.56 | 20.83 | 18.24 | 23.08 |
| Found | 30.9 | 6.9 | 21.1 | 17.7 | 23.1 |

In addition the structure of the compound was confirmed by the $^1$H-NMR spectrum.

Testing the crosslinkability:

The following amounts of a 20% strength by weight aqueous solution of the crosslinking agent (VI) were added to 100 g portions of dispersions 1 and 2 (in each case a–c in the Table) and the final pH was adjusted with concentrated aqueous ammonia.

| Dispersion | Amount of crosslinking agent (20% strength by weight solution) [g] |
|---|---|
| 1 | — |
| 1a | 9.0 |
| 1b | 6.8 |
| 1c | 3.4 |
| 2 | — |
| 2a | 9.0 |
| 2b | 6.8 |
| 2c | 3.4 |

The dispersions were converted into films in the course of 4 days at 23° C. and 50% atmospheric humidity. About 4 cm$^2$ pieces were cut from the 500 μm thick films and were swollen in 100 ml of tetrahydrofuran (THF) over a period of 24 hours at room temperature.

The solvent absorption of the test specimens was determined gravimetrically and is stated in percent. The lower the swelling values, the greater is the crosslinking of the samples.

EXAMPLE 1

| No. | Molar ratio Crosslinking agent/AAEM | pH | THF swelling after 24 h in % by weight |
|---|---|---|---|
| 1 | No crosslinking agent | 6 | 1350 |
| 1a | 0.74:1 | 4 | 580 |
|  |  | 6 | 530 |
|  |  | 8 | 560 |
| 1b | 0.55:1 | 4 | 650 |
|  |  | 6 | 665 |
|  |  | 8 | 605 |
| 1c | 0.28:1 | 4 | 950 |
|  |  | 6 | 1020 |
|  |  | 8 | 815 |
| 2 | No crosslinking agent | 6 | 1060 |
| 2a | 0.74:1 | 6 | 495 |
| 2b | 0.55:1 | 6 | 545 |
| 2c | 0.28:1 | 6 | 880 |

We claim:

1. A compound of the formula

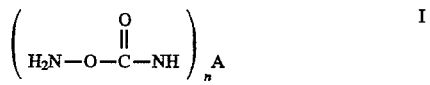

where A is an n-valent organic radical and n is an integer greater than 1, or a salt thereof.

2. A process for the preparation of a compound of claim 1, wherein polyisocyanates, whose isocyanate groups are blocked by oximes or hydroxamic esters are reacted with water and an acid having an acid constant of $>10^{-2}$.

3. A dispersion of solution of a free radical polymer, polycondensate or polyadduct, containing a compound of claim 1.

4. A dispersion or solution as claimed in claim 3, where the free radical polymer, polycondensate or polyadduct comprises from 0.001 to 20% by weight of aldehyde groups (CHO) or keto groups (CO).

5. A dispersion or solution as claimed in claim 3, containing a copolymer as a free radical polymer, wherein the copolymer consists of a) at least one comonomer having at least one aldehyde or keto group, b) from 20 to 99.99% by weight of at least one $C_1$–$C_{20}$-alkyl (meth)acrylate, one vinyl ester of carboxylic acids of 1 to 20 carbon atoms, one vinyl aromatic of up to 20 carbon atoms, one ethylenically unsaturated nitrile of 3 to 6 carbon atoms, one vinyl halide or one nonaromatic hydrocarbon having 4 to 8 carbon atoms at least 2 conjugated double bonds, and c) from 0 to 50% by weight of at least one further ethylenically unsaturated monomer, the content of the monomer a) being chosen so that the copolymer contains from 0.001 to 20% by weight of aldehyde groups (CHO) or keto groups (CO), and the monomers a), b) and c) summing to 100% by weight.

* * * * *